(12) United States Patent
Farah et al.

(10) Patent No.: US 10,952,807 B2
(45) Date of Patent: Mar. 23, 2021

(54) CUSTOM THREE DIMENSIONAL FORMING OF SURGICAL GUIDES

(71) Applicant: SENSO MEDICAL LABS LTD., Nazareth (IL)

(72) Inventors: Maroun Farah, Nazareth (IL); Haytham Sulieman, Haifa (IL); Fadi Saba, Haifa (IL)

(73) Assignee: SENSO MEDICAL LABS LTD., Nazareth (IL)

( * ) Notice: Subject to any disclaimer, the term of this patent is extended or adjusted under 35 U.S.C. 154(b) by 326 days.

(21) Appl. No.: 15/525,151

(22) PCT Filed: Nov. 9, 2015

(86) PCT No.: PCT/IL2015/051079
§ 371 (c)(1),
(2) Date: May 8, 2017

(87) PCT Pub. No.: WO2016/071915
PCT Pub. Date: May 12, 2016

(65) Prior Publication Data
US 2017/0333150 A1    Nov. 23, 2017

Related U.S. Application Data

(60) Provisional application No. 62/077,247, filed on Nov. 9, 2014.

(51) Int. Cl.
*A61B 90/11* (2016.01)
*A61N 1/05* (2006.01)
(Continued)

(52) U.S. Cl.
CPC ........ *A61B 90/11* (2016.02); *A61B 17/00234* (2013.01); *A61B 34/10* (2016.02);
(Continued)

(58) Field of Classification Search
CPC ......... A61B 90/10; A61B 90/11; A61B 90/13; A61B 90/14; A61B 90/16; A61B 90/17;
(Continued)

(56) References Cited

U.S. PATENT DOCUMENTS 6,592,578 B2    7/2003 Henniges et al.
2005/0085714 A1*  4/2005 Foley ................. A61B 17/1735
                                              600/424

(Continued)

FOREIGN PATENT DOCUMENTS

EP         1094760        3/2006
WO      2014002284        1/2014
(Continued)

OTHER PUBLICATIONS

International Search Report of PCT/IL2015/051079 Completed Mar. 10, 2016; dated Mar. 10, 2016 4 Pages.
(Continued)

*Primary Examiner* — Wade Miles
*Assistant Examiner* — Kankindi Rwego
(74) *Attorney, Agent, or Firm* — The Roy Gross Law Firm, LLC; Roy Gross

(57) ABSTRACT

A kit including a medical guide template, and a sterilizable receptacle accommodating the guide template, the kit being configured to allow deformation of the template into an operational medical guide.

19 Claims, 16 Drawing Sheets

(51) Int. Cl.
  *A61B 34/10* (2016.01)
  *A61B 90/14* (2016.01)
  *A61B 90/00* (2016.01)
  *A61B 17/00* (2006.01)
  *A61C 1/08* (2006.01)
  *A61B 34/30* (2016.01)

(52) U.S. Cl.
  CPC .............. *A61B 90/14* (2016.02); *A61B 90/39* (2016.02); *A61C 1/082* (2013.01); *A61N 1/0534* (2013.01); *A61N 1/0551* (2013.01); *A61B 34/30* (2016.02); *A61B 2017/00946* (2013.01); *A61B 2034/105* (2016.02); *A61B 2034/107* (2016.02); *A61B 2034/108* (2016.02); *A61B 2090/363* (2016.02); *A61N 1/05* (2013.01)

(58) Field of Classification Search
  CPC ......... A61B 90/18; A61B 90/20; A61B 90/39; A61B 2090/101; A61B 2090/103; A61B 34/10; A61B 34/20; A61B 34/30; A61B 2034/105; A61B 2034/107; A61B 2034/108; A61C 1/08; A61C 1/082
  USPC ........................................................ 606/130
  See application file for complete search history.

(56) References Cited

U.S. PATENT DOCUMENTS

| | | |
|---|---|---|
| 2005/0106531 A1 | 5/2005 | Tang |
| 2006/0212044 A1 | 9/2006 | Bova et al. |
| 2008/0166681 A1* | 7/2008 | Weinstein .............. A61C 1/084 433/76 |
| 2015/0035206 A1* | 2/2015 | Maggiore .............. B29C 64/00 264/401 |

FOREIGN PATENT DOCUMENTS

| | | |
|---|---|---|
| WO | 2014026706 A1 | 2/2014 |
| WO | 2014176118 | 10/2014 |

OTHER PUBLICATIONS

Written Opinion of ISR of PCT/IL2015/051079 Completed Mar. 10, 2016; dated Mar. 10, 2016 7 Pages.

* cited by examiner

CUSTOM THREE DIMENSIONAL FORMING OF SURGICAL GUIDES

This application is a 35 U.S.C. § 371 national phase application of PCT/IL2015/051079, filed Nov. 9, 2015, which claims priority to U.S. 62/077,247 filed on Nov. 9, 2014. All applications are incorporated herein by reference as if fully set forth.

FIELD OF THE INVENTION

The invention relates to medical devices that include medical guides from deformable materials, guides made by 3-D printing and guides made within sterile receptacles, and systems that manufacture these guides.

BACKGROUND OF INVENTION

Some surgical interventions are performed inside the body with the aid of a surgical guide. In spinal surgeries a correct trajectory for a medical device is usually crucial, whereas in surgeries of small regions in the body an accurate targeting distance from the device to the target is particularly important. In addition, stereotaxic systems may be used in the intervention. Stereotaxy is a minimally invasive form of surgical intervention which makes use of a three-dimensional coordinate system to locate small targets or trajectories inside the body and to perform on them some medical action. In theory, any part inside the body can be subjected to stereotactic surgery, such as cranial, neurological, spinal, dental, orthopaedic, and ENT (ear, nose and throat) systems.

Plain X-ray images, computed tomography, magnetic resonance imaging and other imaging methods can be used to guide the procedure. Typically, the images of anatomical structure (for example, a human brain), are collected and related to a coordinate system. A guide calibrated to the same coordinate system may be used to direct a medical device to the target or along a certain trajectory. In most stereotactic brain surgeries locators/markers/fiducial-points serve as relative locations for the guide engagement.

Adjusting the guide to provide the correct distance of a medical device to a target and/or the correct trajectory within the body can be complex and time consuming. Moreover, in some procedures multiple targets or trajectories must be determined. For example, in spinal stereotactic surgery, multiple trajectories on different spinal segments are used. One option to align the guide includes providing an adjustable instrument guide. However, the adjustments of the adjustable guide require careful manual manipulations which significantly prolong the operation, and might be difficult to perform in some procedures, such as in dental operations wherein the maneuverability is severely limited and the guide parts are miniature. Another option includes providing a customized guide that is fabricated for a particular patient, such that targeting is unnecessary or greatly simplified.

EP 1094760 describes a method for forming a surgical guide (guide) for attaching to a body and providing a reference structure for precisely locating a target within the body, the method including: processing a three-dimensional scanned image of the body, the scanned image including the target within the body and a mounting location of the body; determining a structure of the surgical guide such that when attached at the mounting location of the body the guide provides a reference structure in a determined location and orientation with respect to the target within the body.

One of the method options described in EP 1094760 involves selecting a model of a standard guide and deforming the model to match the model to the target and the mounting location. As further described in EP 1094760, the structure of the guide can be determined in terms of a solid model of the guide which defines the volume enclosed by the surface of the guide. The solid model is computed so that the resulting guide can be precisely attached to the body. The method can then also include fabricating the guide according to the solid model. Clearly, therefore, the "solid" model that is described in EP 1094760 is actually a software representation of the guide.

Some medical procedures, such as deep brain surgery, involve trial-and-error location of the target, which in some operations entails remanufacturing or reconfiguration of the guide or the stereotactic guiding system, as well as resterilization. In such cases, the method described in EP 1094760 does not prevent rescheduling of the operation to a different day.

One object of the invention is to allow reforming a guide quickly enough to allow the operation to continue; preferably a new guide would be formed within mere minutes or even seconds.

Medical robotic systems such as ROSA allow frameless stereotactic procedures and thus does not require fabrication of a guide. Instead, stereotactic reference points for the robot are determined from images and quickly adjusted if the target is discovered to be at another location. However, the robotic system has a number of disadvantages as well: engagement of the robot with the patient is uncomfortable and highly complex; the robot needs to be sterilized before each operation; the robotic system is expensive and occupies a large space in the operating room; the accurate positioning of the system requires considerable skill; the system is dedicated to one patient during one operation session. For operations such as installing screws in the spine the robot needs to be repositioned many times, which prolongs the operation and the time the robot is needed per patient.

The Da Vinci Surgical System is another robotic surgical system, made by Intuitive Surgical. The system is controlled by a surgeon from a console. Although the system can multitask with a number of arms, nevertheless readjustment of positions in real-time throughout the operation requires dedication of the system to the operation and the system has other disadvantages similar to ROSA. The da Vinci system has particularly been criticized for its cost and for a number of issues with its surgical performance. The present invention intends to address these problems.

SUMMARY OF THE INVENTION

It is therefore provided in accordance with a preferred embodiment of the invention A kit comprising:
 a medical guide template, and
 a sterilizable receptacle accommodating the guide template,
  wherein the kit is configured to allow deformation of the template into an operational medical guide.

In accordance with another embodiment, said medical guide template is a curable template bulk.

In accordance with another embodiment, said curable template is cured using UV light.

In accordance with another embodiment, said medical guide template is made of a plurality of components that are capable of being moved relative to each other with multiple degrees of freedom and wherein curable adhesive material is placed in joints between the components.

It is also provided in accordance with another preferred embodiment, a medical guide template configured to allow deformation thereof into an operational medical guide and prevention of collapse thereof during and after the deformation.

In accordance with another embodiment, the template comprising a group comprising of:
  at least one deformable material;
  a plurality of components that are capable of being moved relative to each other, and
  combinations thereof.

In accordance with another embodiment, the template comprising curable material.

In accordance with another embodiment, the deformable material is curable.

In accordance with another embodiment, the curable material is in contact with at least two of the plurality of components.

In accordance with another embodiment, an operational guide is provided that comprises:
  at least one base element capable of engaging body anchoring points;
  at least one targeting element, each targeting element being capable of engaging at least one medical device, and
  connective structural elements connecting the at least one base element with the at least one targeting element;
  wherein the guide allows the medical devices to access at least one target when the at least one base element is engaged with the body anchoring points and the at least one medical device is engaged with the at least one targeting element, and
  wherein the connective structural elements are deformed.

In accordance with another embodiment, the deformation is based upon fiducial-points for the operational guide engagement, and wherein the guide is attachable to anchoring points that are attached to the body, the anchoring points being in a measured relation to the fiducial-points.

A system is also provided comprising:
  markers;
  a computer;
  a scanner;
  a forming robot, and
  a medical guide template, and
  a medical device;
wherein:
  the markers represent physical reference points on a bodily part;
  the scanner is capable of scanning the bodily part with the markers thereon;
  the computer is operationally coupled to the scanner and forming robot, and configured to allow to allow the computer to:
    receive an image from the scanner,
    establish a relation between the markers and a target or trajectory identified on the image, and
    establish forming data transferred to the forming robot;
  the robot is capable of deforming the template into an operational medical guide adapted to allow the medical device to be aligned with the target or trajectory.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention, in this regard, no attempt is made to show structural details of the invention in more detail than is necessary for a fundamental understanding of the invention, the description taken with the drawings making apparent to those skilled in the art how the several forms of the invention may be embodied in practice.

The present invention will be understood and appreciated more fully from the following detailed description, taken in conjunction with the drawings in which.

Figure 1:
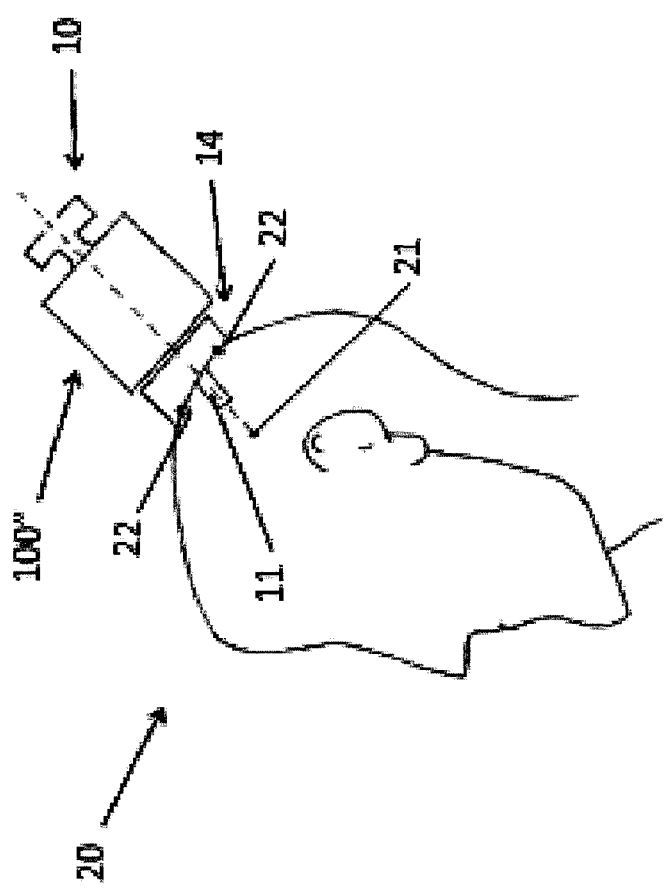
FIG. 1 schematically illustrates a probe extended from a medical device along a trajectory that leads the probe to a target in a patient using a medical guide in accordance with an exemplary embodiment.

While the disclosure is amenable to various modifications and alternative forms, specifics thereof have been shown by way of example in the drawings and will be further described in detail herein below. It should be understood, however, that the intention is not to limit the disclosure to the particular embodiments described. On the contrary, the intention is to cover all modifications, equivalents, and alternatives

DETAILED DESCRIPTION OF THE INVENTION

According to one aspect, medical guide templates comprising deformable materials and/or deformable structures are provided, that become operational guides after deformation.

Some guide embodiments and systems for production thereof are provided, that do not comprise deformable materials, but rather comprise components that can be moved to deform into a guide and prevent collapse of the guide during deformation.

Some guide embodiments are provided that are not created by deformation, for example they are created by 3-D printing, as further discussed below.

According to another aspect, forming systems and methods for preparing the operational guides from the guide templates are provided.

According to yet another aspect, sets comprising various deformable guide templates are provided.

Yet another aspect concerns kits comprising receptacles containing therein sterilizable medical guide templates, and systems and methods to produce them.

Reference is now made to FIG. 1 schematically illustrating a probe extended from a medical device along a trajectory in accordance with an exemplary embodiment. As schematically shown in FIG. 1, a probe 11 is extended from a medical device 10 along a trajectory (broken line) that leads the probe 11 to a target 21 in a patient 20. A medical guide 100" helps make the access of the probe 11 stable, planned and accurate. The proper access entails appropriate trajectory alignment of the guide 100", which in turn requires the guide 100" to have a suitable geometry. However, since both the patient's features and the targets/trajectories widely vary between patients, guides of different geometries are required in different operations.

Various solutions have been proposed to adjust the geometry of the guide or to customize the geometry to an operational guide for a particular operation. However, to the best of our knowledge, none of the solutions provide operational guides that are made of materials or structures that can be deformed to their final form in the operation room before or during operation. The operational guides in accordance with the embodiments taught in the present disclosure are made from deformed templates that can be rapidly formed.

Figure 2:
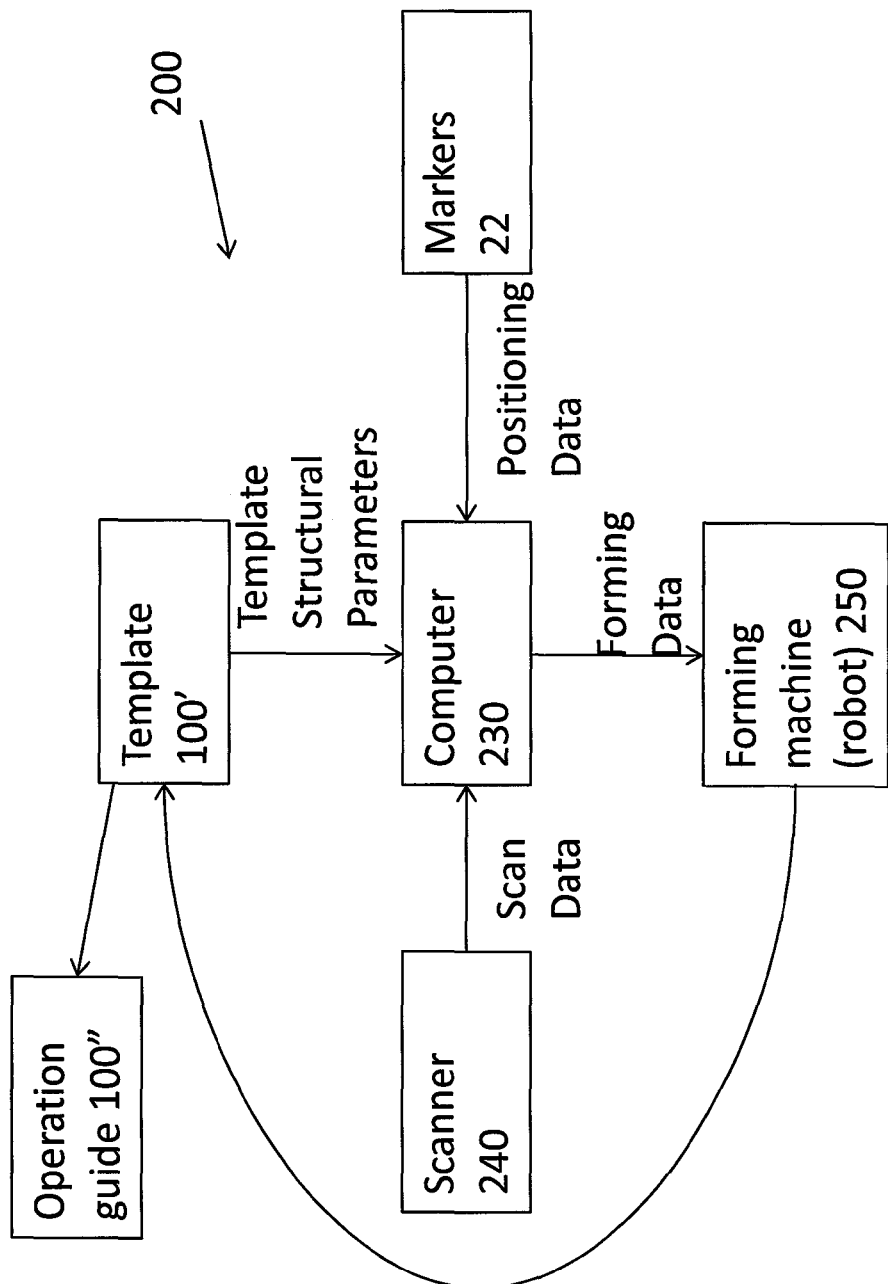
FIG. 2 depicts in a block diagram a method for formation an operational medical guide in accordance with an exemplary embodiment.

FIG. 2 depicts in a block diagram a method embodiment for formation of an operational medical guide of a template 100", by a guide forming system 200. Major components in the forming system 200 are: a computer 230, a scanner 240, and a forming robot (or machine) 250. Preferably, computer 230 receives information from 3 sources: the scanner 240 that scans the bodily part, the template 100" that was chosen for the particular procedure, and the type of markers 22 or anchoring element 14 that were used that represents physical reference points on that bodily part. The information is being calculated to establish forming data that is being transferred to a machine such as a forming robot 250 that deforms the template into a guide that can be used in the operation.

It should be emphasized that the method as described herein can be performed within the operation room or near it and the production of the guide is being made on the site and within a very short while so that it can be utilize during the operation without the need to perform earlier fabrication in a remote location as being performed in the prior techniques.

It should also be emphasized that the element and process described in FIG. 2 does not have to be performed at the same time and can be done in different occasions. For example, engaging the markers on the patients (e.g. through implantation or through a sticker label on patient body) or scanning of the patient can be performed before the forming process is done, also forming of the template guide into an operational guide can be performed hours, days or even weeks before the operations in.

Optionally, the disclosed method can be performed in a sterile environment. This option even promotes the possibility to perform the formation of the guide within the operation room since it makes the sterilization process redundant.

Referring back to FIG. 1 as well, markers 22 or anchoring elements are engaged with the patient's body 20 preferably proximal to the target 21, preferably on hard surfaces that allow the engagement to be steadfast. The scanner 240 is employed to obtain an image that includes indications of the markers 22; the target 21 and the trajectory 11 are determined from the image as well. As mentioned herein before, the computer 230 is fed with the image as well as the structure parameters of a template that is chosen to accord with a specific operational procedure. The computer 230 calculates forming data from the image and the structure parameters. The forming data is conveyed to the forming robot 250 that deforms the template 100' to an operational guide 100" so that when the operational guide 100" is engaged with the markers 22 or the anchoring element 14, a medical device 10 is properly aligned with the target 21, E.g. passing through trajectory 11, reaching exactly to target 21. In other examples multiple parallel trajectories and targets on those trajectories can be accessed correctly with the same operational guide. In other examples, trajectory can be a restricted planar area on an imaginary plain.

Figure 3:
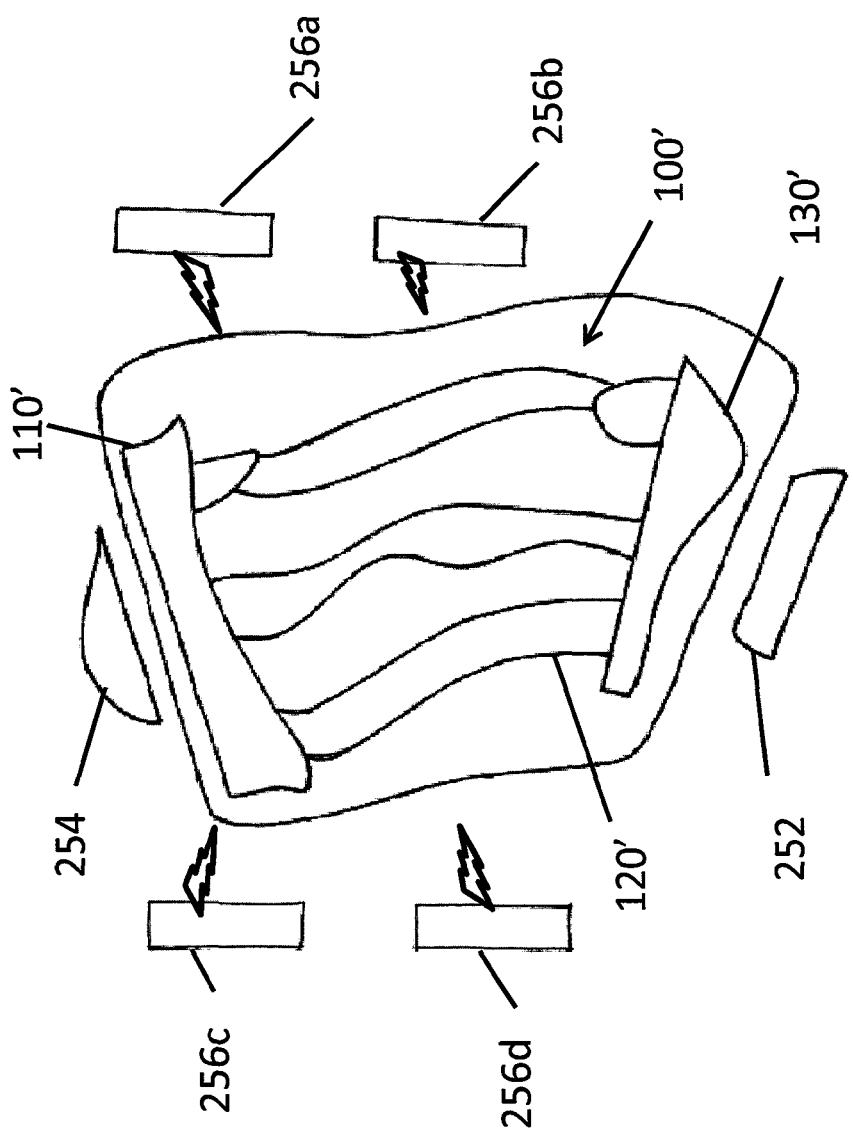
FIG. 3 schematically illustrates a template in accordance with an exemplary embodiment going through deformation.

FIG. 3 schematically illustrates deformation of a template embodiment 100'. The template 100' comprises a targeting element 110', connective structural elements 120', and a base element 130'. The device 10 (see FIG. 1) the operational guide 100", and the anchoring element 14 may each have an aperture (not shown), through which an electrode or other device such as a guide tube, an optic fiber, a biopsy needle, drill, saw or an ablation device, and/or radiation such as noninvasive gamma rays, can be introduced into a patient's brain, internal organ, or a joint, etc. The targeting element 110' is intended to be coupled to the medical device 10, the base element 130' is intended to be coupled to the markers 22 or the anchoring element 14, and the connective elements 120' connect the targeting element 110' to the base element 130'.

A certain template from a variety of templates may be used in various surgeries, such as hip replacement, knee replacement, ENT, dental, spinal procedures etc. In some optional embodiments, multiple targets can be targeted with the same template, which comprises multiple base elements and/or multiple targeting elements. For example, such templates may be required in epilepsy surgeries, and in spine surgeries.

Preferably, a forming machine such as a robot includes an upper arm 254 that is engaged with the targeting element 110' and a lower arm 252 that is engaged with the base element 130'. The template 110' is either malleable or is made so by the employment of a plasticizer, specifically to FIG. 3, a heater 256, which is controlled by the computer 230. Optionally, the robot can be provided with a controller that controls the heater 256.

Since the template 100' is made of materials or made from parts having multiple degrees of structural freedom, the robot then repositions the targeting element 110' with respect to the base element 130' of the template 100', to form an operational guide (not shown) of an appropriate alignment.

Typically, the connecting elements 120' are malleable components. Other means that produce an effect of making the template malleable may be used: for example, lighting with a corresponding wavelength; passing electric current with an electric device through a suitable material. Other exemplary embodiments may comprise glue that is uncured before deforming the template and quickly cures after the deformation, as will be further discussed below.

Some embodiments of such templates are mechanically deformable templates where UV glue is applied in strict areas (typically various joints), and the glue is cured after a required shape is assumed, thereby providing a rigid required form. Such glue may be applied at the factory where the template is manufactured, and cured long thereafter, close to the time of use. Suitable glues may allow the curing to be performed even years after being applied.

Some template embodiments comprise deformable components that are curable. In some system embodiments the curing can be done by the robot that does the deformation; in other system embodiments another component of the system performs the curing. In preferred embodiments the complete process of preparing the operational guide takes about 10 s. Therefore an operation can essentially continue uninterrupted even when during the operation physicians discover that a new customized guide is required. The curing method and apparatus are selected according to the malleable material that is selected. The curing can be for example cooling; UV radiation; exposing the template to oxygen, etc.

According to another aspect, a set of deformable templates are provided, each template having a different structure such as length and/or angle of the structural elements relative to the base element. For each medical procedure, a template can be selected from the set that requires minimum time to prepare. Typically, the structure of this selected template is closest in alignment to the required structure.

Some kits may comprise deformable templates having other characteristics such as strength of material that vary between the templates. The template for use may be selected in such kits according to considerations other than the minimum time required to prepare, or according to multiple considerations that may be selectable by the operating physician.

In some embodiments, the preparation includes sterilization of the template and/or the operational guide prepared therefrom or maintaining the sterility of the template since usually the desired guide should be delivered to its use in a sterile manner to be used in a surgical procedure.

Figure 4:
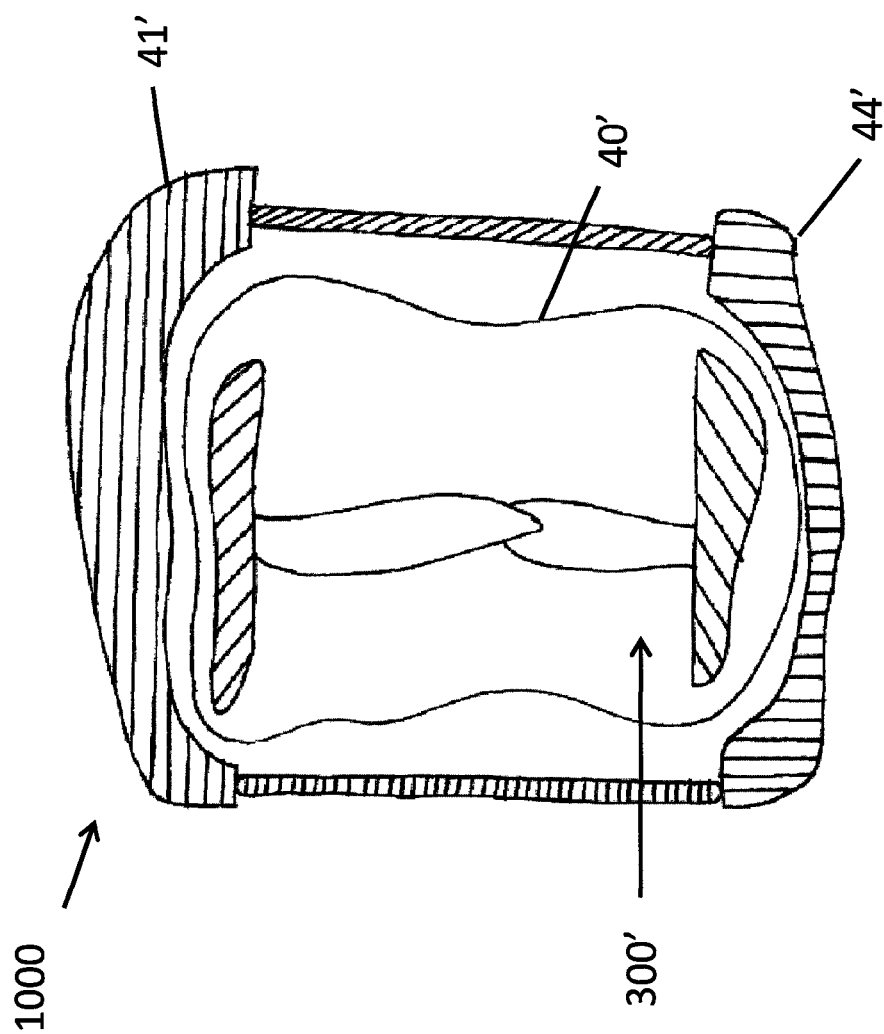
FIG. 4 describes a kit comprising a template that is packaged in a sterilizable bag in accordance with an exemplary embodiment.

Reference is now made to FIG. 4 that describes a kit 1000 comprising a template 300' in sterile condition is packaged in a sterilizable bag 40' that can provide a sterile barrier against contamination of the template 300' and allows preparing the operational guide even in the operating room. The bag 40' is configured to allow the forming system to form an operational guide while maintaining the sterility of the template 300'.

However, some kit embodiments (not shown) comprise a bag that is not sterilizable, but rather is configured to otherwise allow the guide to be protected, for example from dirt, scratches, blows, tampering etc.

A first element 41' extends from the bag 40' and is attached to one side of the bag 40', for example glued onto the sterile bag 40'. In other embodiments the first element can alternatively be attached through a coupling between an external cap and an internal base or targeting elements with the bag between them. A second element 44' is attached to another side of the bag 40'.

Some embodiments comprise a sterilizable bag and a template therein, and further comprise at least one modifier element on or in the bag that can be engaged with the forming system. These modifier elements may be the targeting elements and/or the base element of the template or may be another component that is not part of the template and merely serves to couple the template with the forming system. The modifier elements are each configured to allow one or more of the following:

Mechanical engagement of the template, for example with the forming system, that allows immobilization of parts of the template that are programmed to remain so during the deformation of the template, and deformation of parts of the template that are programmed to deform during the deformation.

Transfer of force and/or energy from the forming system to the template. Such transfer may include conversion of the force/energy from one form into another; for example, the connective structural elements may comprise or have therein or thereon coils that are electrically inductable to heat the structural elements and deform them to their programmed form in the operational guide.

In yet other embodiments, the deformation does not require a modifier element for transfer of force and/or energy. For example, the forming system may comprise UV-radiating means that can be focused on UV-deformable components of the template. In some embodiments there is no need for modifier elements for mechanical engagement as well. The latter embodiments deform into the aligned form by the remote application of energy by the forming system to the template.

In some embodiments, the bags are made of a material that can generate heat under the influence of UV light radiation or radiation at another wavelength.

Some deformations require application of considerable energy to the template. The applied energy might cause application of a great amount of heat on the template that might adversely affect the template from prolonged exposure to heat. Therefore, some bag or template embodiments further comprise heat-removing means that facilitate removal of heat from the template. Such means may be selected from: radiation-deflectors such as mirrors; mechanical devices such as fans inside the bag that blow air inside the bag to outside the bag via a one way-valve and/or fans that blow air over the bag; compositions inside the bag that can react in a endothermic reaction that can be induced to occur during or after the deformation, and combinations thereof. The template may further comprise articles of low heat-conductivity that can help isolate the parts that are not intended to be deformed from heat. Multifocusing of the radiation, i.e. using multiple light sourcing on one area, may help to quickly heat a very specific area with minimal heating outside the selected area.

Depending on the treatment methods and curing methods used to reform the template into its soft state and set the template in its final aligned form, respectively, the sterile bag can include an indicator thereon or therein to indicate the reliability of the treatment, e.g. a UV indicator that can indicate if the template absorbed an excessively high level of UV light before being brought to the forming system; meaning that if the target curing method relies on UV radiation then the template was corrupted. Oxygen may be introduced into the bag via a septum or one-way valve to cure and an oxygen indicator can be used to follow the curing. Other indicators like temperature can also be included to indicate if there were high temperature events that invalidated the target forming abilities.

Some kit embodiments comprise similar bags or other suitable receptacles such as jars, and suitable devices other than medical guides, that can similarly be placed within the receptacle and formed therein.

Some guide embodiments do not serve for targeting but rather for other purposes for example attached to a patient's rigid body part such as a bone. Some embodiments are formed that allow aligning a surgical tool or a medical device attached thereto to a certain trajectory pointing to a body target that has a known geometrical relation with the bone.

Some operational guides are customized to juxtapose bones or optionally space them apart as is required. The process comprises for example: imaging the bones in order to record their shapes, dimensions and other physical features; subsequently computing alignment and spacing of these bones in relation to each other; selecting a template guide, determining deformation data of said template guide; deforming the template according to the data into a final formed operational guide that when attached on either ends to bones aligns the bones, and optionally determining a fixed space between them exactly as determined by the initial plan. In some operations before the imaging is performed, the sides of the bones that are to be attached to the template are cut and processed to suit and couple to the attachment mechanism of the template, Some guide embodiments comprise places for more than two bones; or even for only one bone; some embodiments further comprise joints and/or moving parts; however, an important aspect is that the guides can be created from a template by executing deformation based on data deforming the object into its final orientation and shape.

A customized operational guide' may sit on screws that are attached to patient bones; these screws can also be used as markers in order to geometrically relate the target and the base of the customized guide allowing the determination of the shape of the customized guide.

The guide may sit directly on bur hole that is drilled in the patient's bones or may be attached to the skull or sit on another object that is sitting on patient skull or other rigid body parts and attaches to the bur hole or the other object at only one point, or to multiple points in a certain predetermined plain. The form of this guide is determined after imaging is made; deforming information is determined that is needed to deform the object so that the targeting and the alignment are operable through the guide; the deforming information is sent to the forming machine that will deform the generic template into the final custom guide; this guide will then be attached to the hole in the bone or to another object attached to the bone in order to direct a surgical instrument through a planned trajectory to the certain target.

The surgical tool does not have to be a tool that penetrates the patient body; instead it could be a tool that needs only to correctly be aligned to patient anatomy; this will be needed if for example if an energy or other non invasive waves are needed to be transferred to a certain target.

Figure 5A:
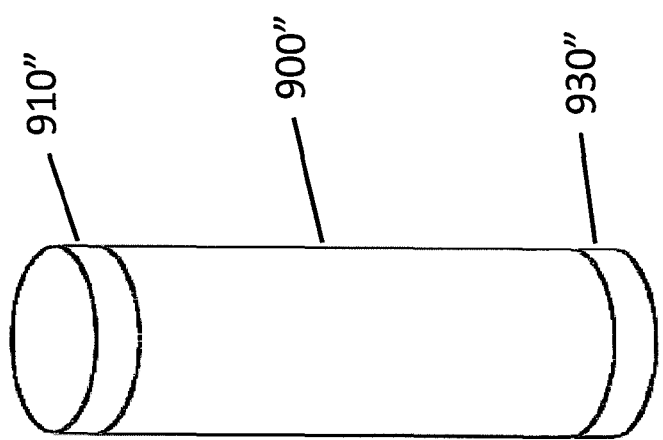
FIG. 5*a* schematically illustrates an example of a generic template having one leg to couple to rigid body parts of a patient in accordance with an exemplary embodiment.
Figure 5B:
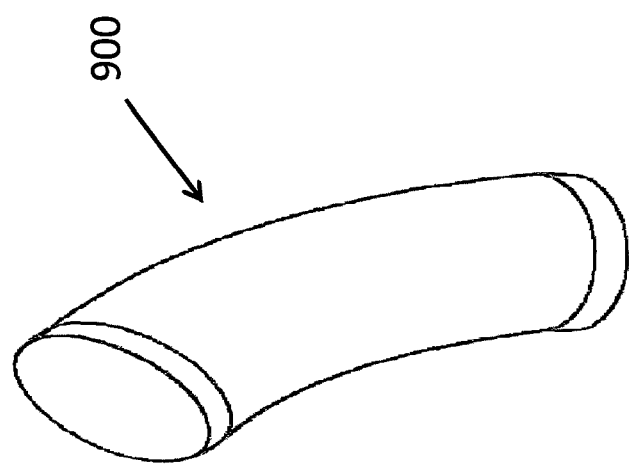
FIG. 5*b* schematically illustrates the template shown in FIG. 5*a* after deformation.

Reference is now made to FIGS. 5a-5b that schematically illustrate another example of a generic targeting and alignment template 900", FIG. 5a, that is formed into an operational guide 900, FIG. 5b. The desired trajectory of the medical apparatus into the patient body could pass through the operational guide or even any other axis determined by the shape of the guide. The generic template has one leg to couple with rigid body parts of the patient (or to attach to other object assembly); a medical apparatus can sit on the upper side targeting element 910" while attachment to rigid body parts could be made to the base element 930".

Figure 5C:
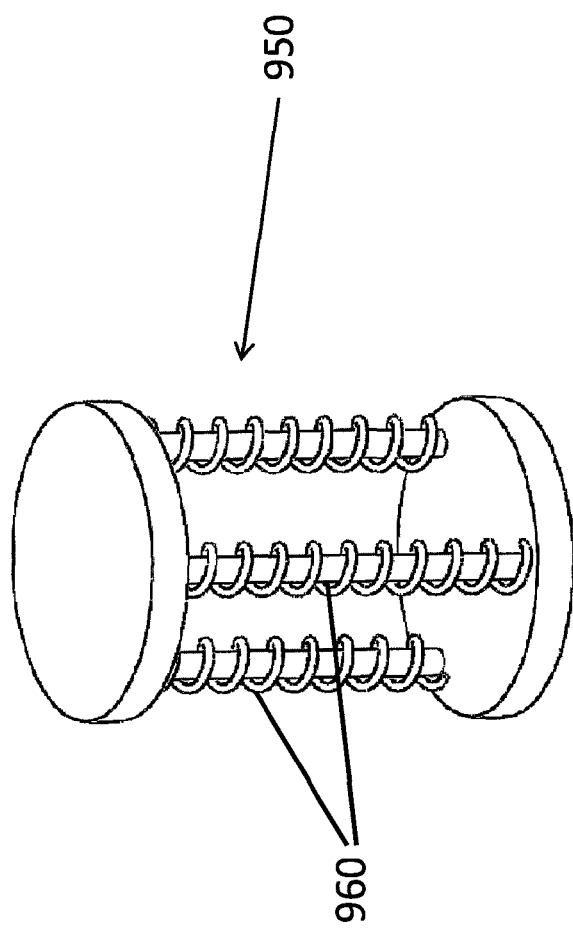
FIG. 5*c* schematically illustrates a template provided with an enhancement in accordance with yet another exemplary embodiment.

FIG. 5c illustrates an optional template 950 with a resilient frame such as a springs 960 that prevents the resulting guide from collapse during the deformation process. Other such exemplary embodiments will be explained herein after.

Figure 6A:
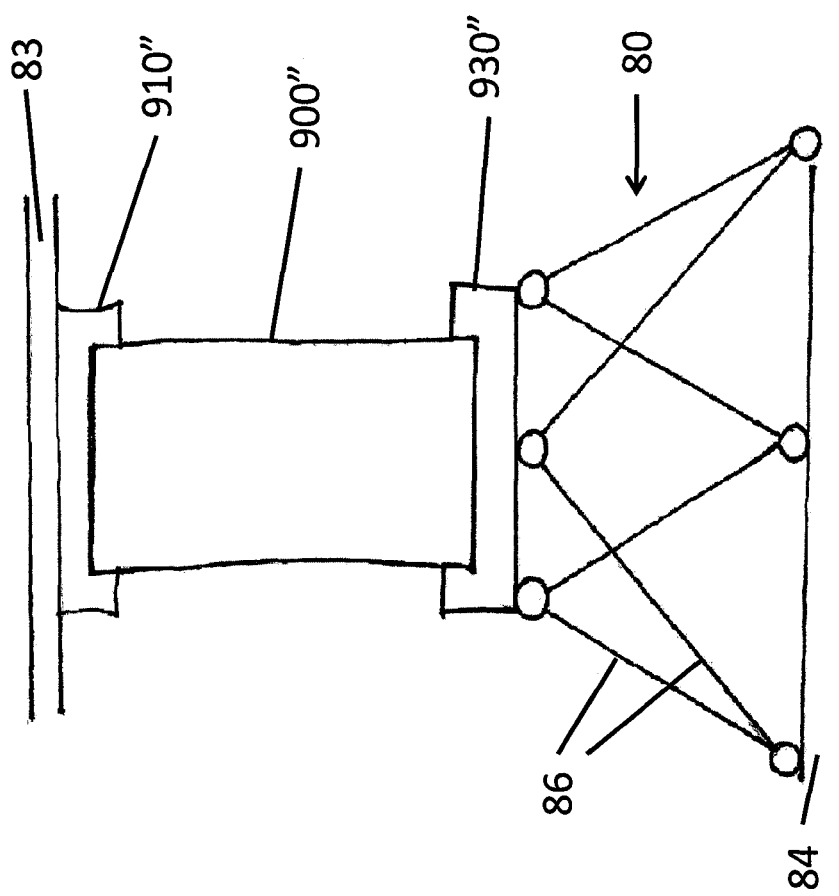
FIG. 6*a* schematically illustrates a generic template in accordance with an exemplary embodiment, placed in a forming system.

As shown in FIG. 6a, the template 900" is inserted into the forming machine 80; here we only show an example of important components of an exemplary machine 80 that comprise an upper attachment plate 83 with a special mating place to the targeting element 910" of the template 900" and a lower plate 84 at the base of the machine 80 which attaches to the base element 930" of the template 900". Subsequently the machine 80 may initiate a phase turning the template 900" into a malleable object 901, shown in FIG. 6b, for example by heat or humidity or other means as indicated herein above, or the template 900" may be innately malleable before any deformation actions, in which case this step may be omitted. Deforming data and instructions are sent to the machine 80. Subsequently either the upper plate 83 or the lower plate 84 or both of them together will move according to deformation instructions until they align the upper plate 83 and lower plate 84 in relation to each other according to the desired final form of the template.

Arms 86 connect the upper and lower plates through the template so as to set the distances between these plates; and thus determine the plates' orientations and place in space. The arm length may be adjustable e.g. by telescopic arms with a length determined by PC/controller; or by a leading screw that is rotated setting the length of the arms.

Figure 6B:
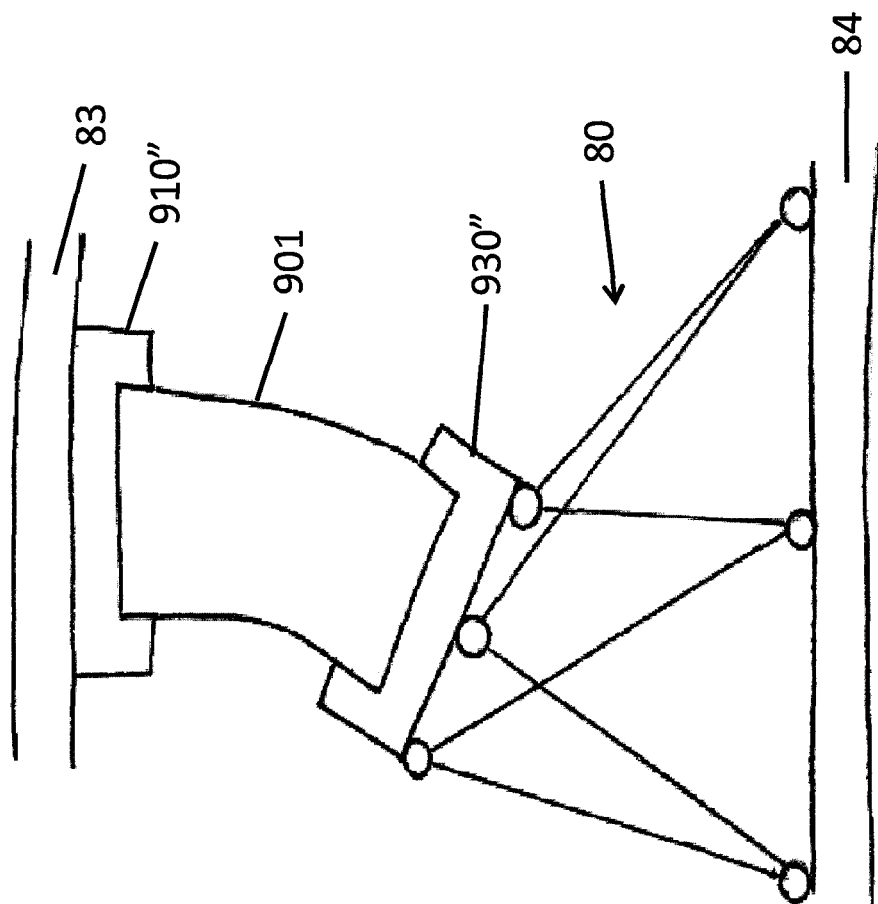
FIG. 6*b* schematically shows the generic template shown in FIG. 6*a* after being deformed.

After the upper plate 83 and the lower plate 84 reach their final positions and orientations as shown in FIG. 6b, according to deforming instructions, a curing cycle will be made by the forming machine 80 or by another apparatus in the forming system that will turn the object into a rigid targeting component assuming the final required shape.

Other types of robots can be employed in order to assist the process without limiting the scope of the present invention. Another robot will be described herein after, however, other possibilities are possible.

Figure 7:
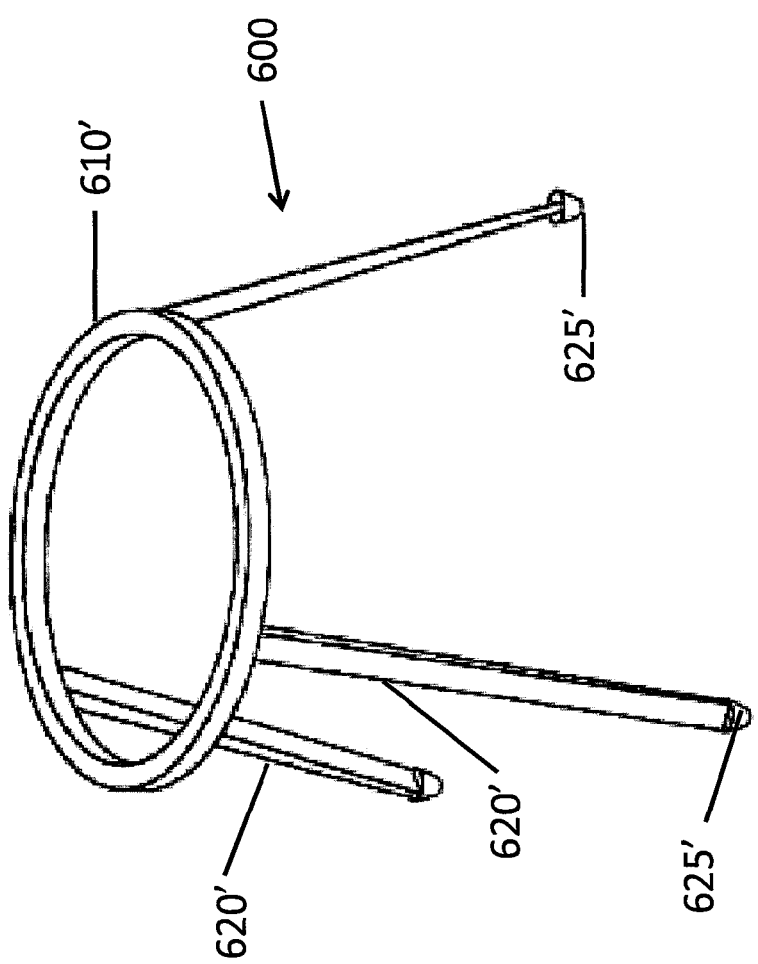
FIG. 7 illustrates an example of another deformable template in accordance with an exemplary embodiment.

Reference now is made to FIG. 7 which schematically illustrates another guide that has three attachment legs 620'; each leg 620' ends with a lead end 625' which in this case each leg should be deformed to exactly align with the anchoring points, screws or element. In general the number of the attachment legs is at least one leg. The targeting element 610' of the template 600' should be coupled to a medical and surgical apparatus, whereas the legs 620' may be coupled to a patient's rigid body parts e.g. bones.

Usually the generic template 600' cannot be used as is for targeting or alignment of a surgical tool to the exact trajectory or target; instead the template first needs deformation.

Figure 8:
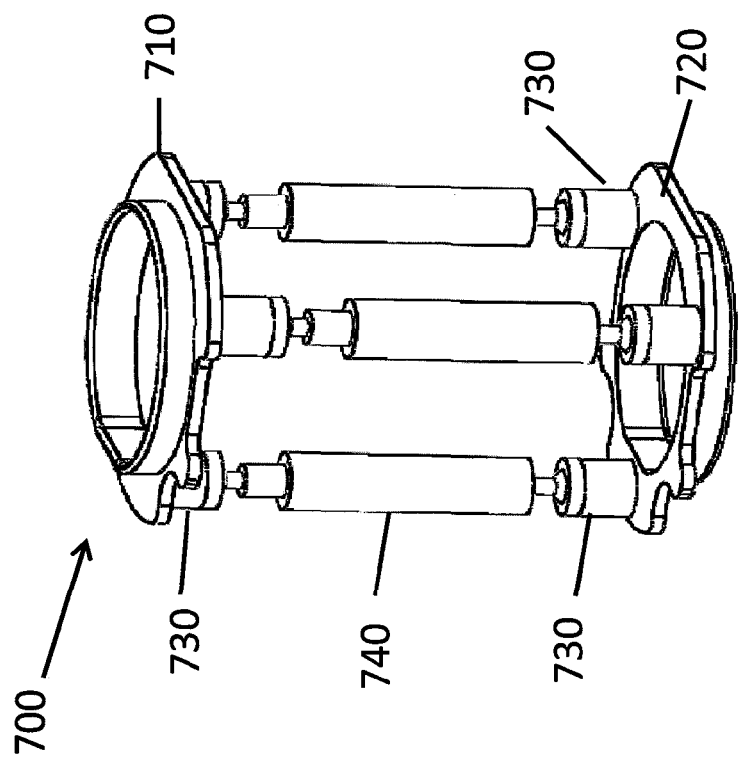
FIG. 8 depicts another template in accordance with an exemplary embodiment.

Reference is now made to FIG. 8 depicting another template in accordance with an exemplary embodiment. Template 700 is made of several parts that are engaged with each other with multiple degrees of freedom, wherein between joints of the parts, glue is provided and confined. Glue is merely an example, other methods of fixation between parts can be employed. The glue is uncured so the degrees of freedom are maintained. Similarly to previous shown embodiments, a base 710 and a top 720 plates are provided so as to be attached to a forming machine or when template is presented inside a bag base 710 and top 720 plates are provided so as to couple to a medical device (not shown) and to be attached to external caps (not shown) that in turn attach to a forming machine where the bag is in between. Joints 730 are provided on the base and top plates so that connecting rods 740 can be jointed to the base and top plates. The connecting rods 740 are preferably telescopic arms that can be fixed into a certain length. As can be understood, the template is fully flexible, regarding orientation and length.

Figure 9:
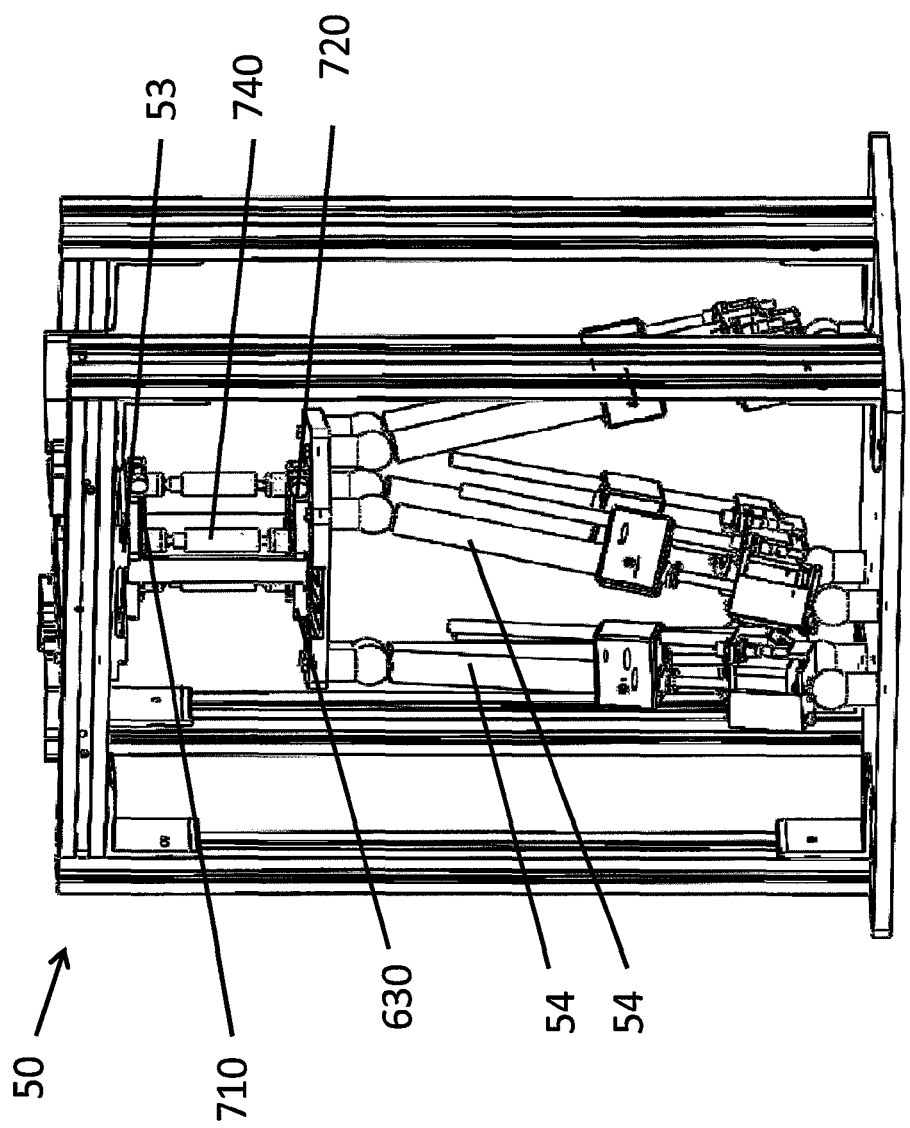
FIG. 9 shows the template shown in FIG. 8, placed within a guide-forming machine in accordance with an exemplary embodiment.

The template as shown in FIG. 8 is inserted in a machine 50, as shown in FIG. 9. The machine 50 comprises the illustrated components: upper attachment fixation 53, and robotic arms 54 that hold the base component 630' of the template 700.

Once the template 700 is inserted in the deforming machine 50 between upper fixation 53 and base component 630, the machine 50, using the movable arms 54 will place the template 700 in the desired and calculated positioning and orientation. After the template gains its final positioning, a phase or a cycle turning the template 700 into a rigid guide is initiated.

Optionally and additionally, instead of starting with a soft template having multiple degrees of freedom, the template can be formed from a rigid material that can be softened, for example by heat or humidity or other means and only then, deformed into the desired orientation. In other embodiments (not shown), one robotic arm sequentially passes over every telescopic leg (connective element), moves it and locks it (from any further movement).

As indicated, the machine 50 preferably allows independent movement of each arm 54. Such movement can be obtained by coupling for example 6 motors to each robotic arm 54. After each robotic arm 54 reaches the final position and orientation, then a curing cycle will be made by the forming machine 50 that will turn the template 700 into a rigid guide assuming the final required shape. This cycle can comprise a cooling cycle and/or a heating cycle or a UV curing cycle—the deforming steps depend on the physical and chemical structure of the template 700 and the mechanisms that are effective in making the template 700 soft or rigid.

In another example, template 700 is inserted in the deforming machine 50 between upper fixation 53 and multiple robotic arms (not shown). These robotic arms should be able to make all movements required to reach to a final form according to data sent by the PC. For example, each robotic arm should be able to determine the vector orientation of the leg ending attached thereto, and then move the centre of the leg ending to the correct place.

It should be noted that when a kit as indicated herein before, where the template is placed within a bag in sterile conditions, the robot is planned to work over the template while the bag is staying intact during action and after. The fact that a bag is being used should not harm the process.

In some of the guide-forming embodiments, jigs maybe used to accurately place the templates inside the bags coupling them to external caps during the production process; after a template is appropriately positioned in the bag the jig can be used to firmly engage the template from outside the bag, with upper and lower caps or similar engagement means that preferably have contours that closely match contours on the template, typically on components of the template most proximal to the walls of the bag. Some templates are deformed without being placed in a receptacle such as a bag. These templates nevertheless may require handling with suitable engagement means as described above for insertion and/or removal into and/or from the forming machine, in particular when the template, before and/or during deformation, is very malleable and might be overly or wrongly deformed as a result of handling.

Figure 10:
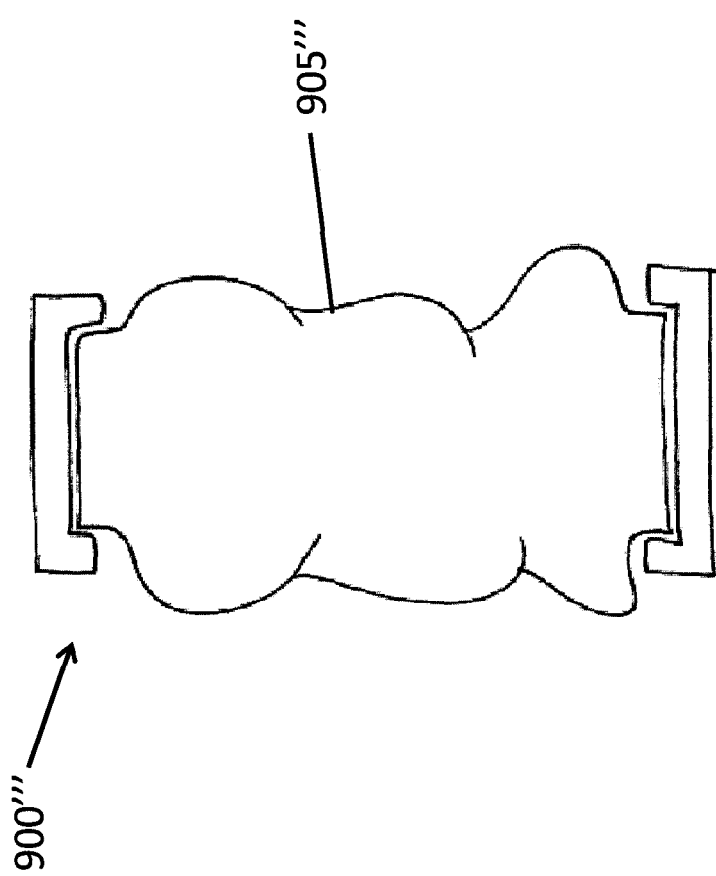
FIG. 10 depicts an embodiment built from bags hat contain for example mixtures of glue and other materials or just glue or other materials that can transform the template into a rigid object in accordance with an exemplary embodiment, FIG. 11 schematically depicts an operational guide that is formed to conform with the complex contours of the gum or a tooth/teeth of the patient in accordance with an exemplary embodiment.

Reference is now made to FIG. 10 schematically illustrating examples of internal structures of the templates; FIG. 10 depicts an embodiment 900''' built from bags 905''' that contain for example mixtures of glue and other materials or just glue or other materials that can transform the template 900''' into a rigid object by heating or by cooling or by UV light, by materials that harden when mixed together, or other means described above. In this example components of the template 900''' that are designed to attach to the forming machine (not shown in FIG. 10) are designed to be rigid while the bag 900''' can be made from flexible materials. The deforming may involve applying stress to the template 900''' (its legs and other elements of its body) to obtain the appropriate form. This stress can be in the form of stretching a certain element in the structure, trying to press on it to reduce its size or trying to bend it or even twist it.

The template may be built from a perforated structure that can withstand the mechanical stresses put on the structure during the deforming process. The internal structure should be designed in a way so that the structure or portions from it do not break, fracture, collapse, crush or assume any final form that does not have enough strength to withstand the final mechanical forces and stresses that will be encountered during the application and use of the operational guide. The guide can be also created from materials that will become soft when exposed to heat then forming can begin; at the end of the forming a curing cycle (for example cooling) will be initiated in order to make the object rigid in a final desired form.

Filling materials (e.g. glass fibers, small plastic parts) can be used to fill the template deformable body for example for the purpose of establishing a structure lowering the amount of expensive curable materials and for other purposes such as enforcing the final shape of the structure or lowering the amount of time needed to cure the template.

Some preferred template embodiments are made from materials that are flexile and soft during the forming phase and rigid after a curing phase, remaining in the rigid phase all through the use and application of the object. For example the materials comprise polycarbonate that becomes soft in high temperature and then rigid again at a lower temperature; another example could be a template that is internally built from rings, wherein it is easy to adjust the legs' of the template and even include UV-curable glue; when the template is formed in desired form then UV radiation will be applied on the deformed template, forcing the glue to cure and turning the deformed template into a rigid form, an operational guide.

Some embodiments comprise a mechanism in the template wherein once everything in place locking screws are screwed by the forming system, forcing the template to lock in a certain desired form. The locking can be by press locking, i.e. locking a moving mechanism by pushing a pin.

To prevent undesirable collapse of connecting structural elements as a result of the deformation of the templates, some template embodiments comprise supporting means for the structural elements, as shown in FIG. 5c.

Structural elements may comprise various resilient means that help prevent collapse the structural element during deforming of the templates such as a malleable and curable rod inside a spring; a structural element comprising a spring inside a deformable and curable sleeve; a spring inside a deformable and curable rod; or a first spring positioned within a second spring, or even a structural element in accordion-form.

The structural elements may comprise rigid elements that allow the desired deformation without the collapse: a telescopic structural element comprising two cylindrical rods for example. The element may comprise a resilient locking pin which may be brought to a groove or hole to lock the element. Each structural element may comprises beads with a wire or string passing therethough that is controllable by the forming system. The wire/string is held fast at the distal end of the structural element, for example a knot is tied on the last bead, and pulling the wire/string causes the structural element to bend. In some embodiments the string/wire can be pulled in various directions in order to allow various deformations of the template.

An advantage of templates without curable elements is that they are typically easily reverted to their original form, or can be easily converted to yet another form, i.e. they are generally more amenable to multiple uses. Moreover, there is less of a problem of removing excess heat after the deformation. However, the curable templates may more easily conform to complex geometries that are desired.

A structural element may comprise an internally slotted head that allows two rods to slide therein. A lock can be employed to affix the rods to the head when the template assumes the desired form.

Figure 11:
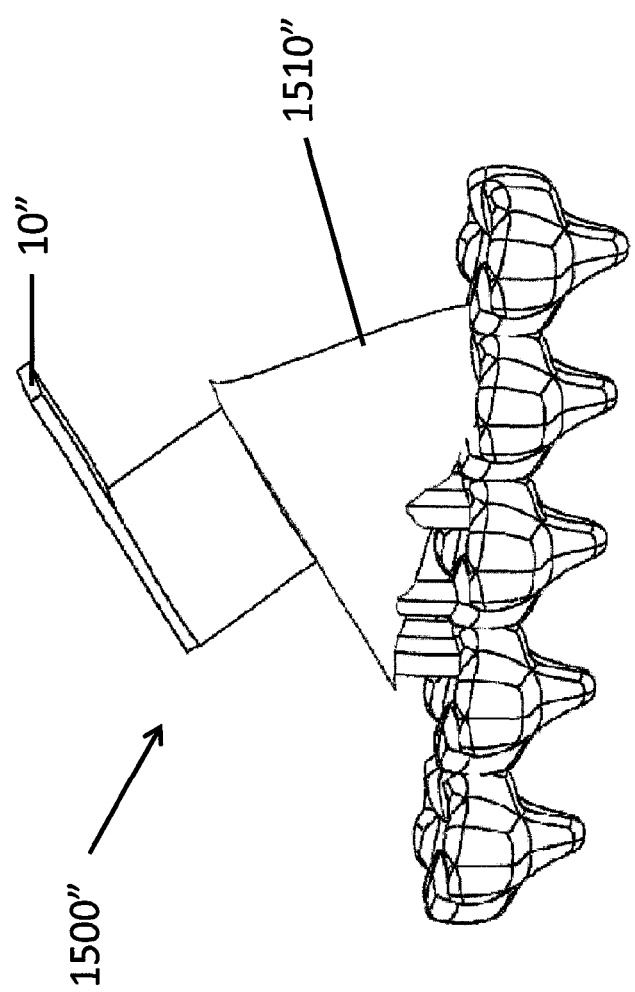

One particular application of the deformation of templates into operational guides is for dental procedures such as installation of dentures. FIG. 11 schematically depicts an operational guide 1500" that is formed to conform with the complex contours of the gum or a tooth/teeth of the patient. A targeting element 1510" may serve both to direct a treatment device (not shown) to the target 10" and as a handle to assist in correct placement of the guide 1500" on the gums or a marker placed thereon. Due to the small size of the templates, some embodiments may be deformed and cured in-situ. However, as opposed to the methods described above, usually first the malleable base component of the template is conformed in shape to the surface of an oral region adjacent to the target, and only then an image is taken with the template in place, the template is removed from the oral cavity and deformed (without altering the shape of the base component) and reintroduced into the oral cavity to the appropriate location therein.

In another embodiment, the base remains in the oral cavity and a miniature template is deformed and then attached to the base during operation.

As an example, two curable materials can be used for the combined template and base, each is cured in a different method. During curing of the base, a first curing method is used and during curing of the template another curing method is used. Alternatively, one curing material is used, but care should be given as to shield the curing material in the template portion during the curing of the base.

According to another aspect, it is important to note that in dental guides and sometimes in other guides for other indications (e.g. spine), multiple guiding elements can be embedded in the template and aligned correctly within the same template by multiple robotic deformations steps. In the purpose of directing surgical tools in different trajectories according to plan when the guide becomes operational. In such cases where deformation is done serially by the forming machine certain shielding should exist to limit the spread of the curing mechanism into neighboring guiding elements that are still unaligned during the deforming process.

Figure 12:
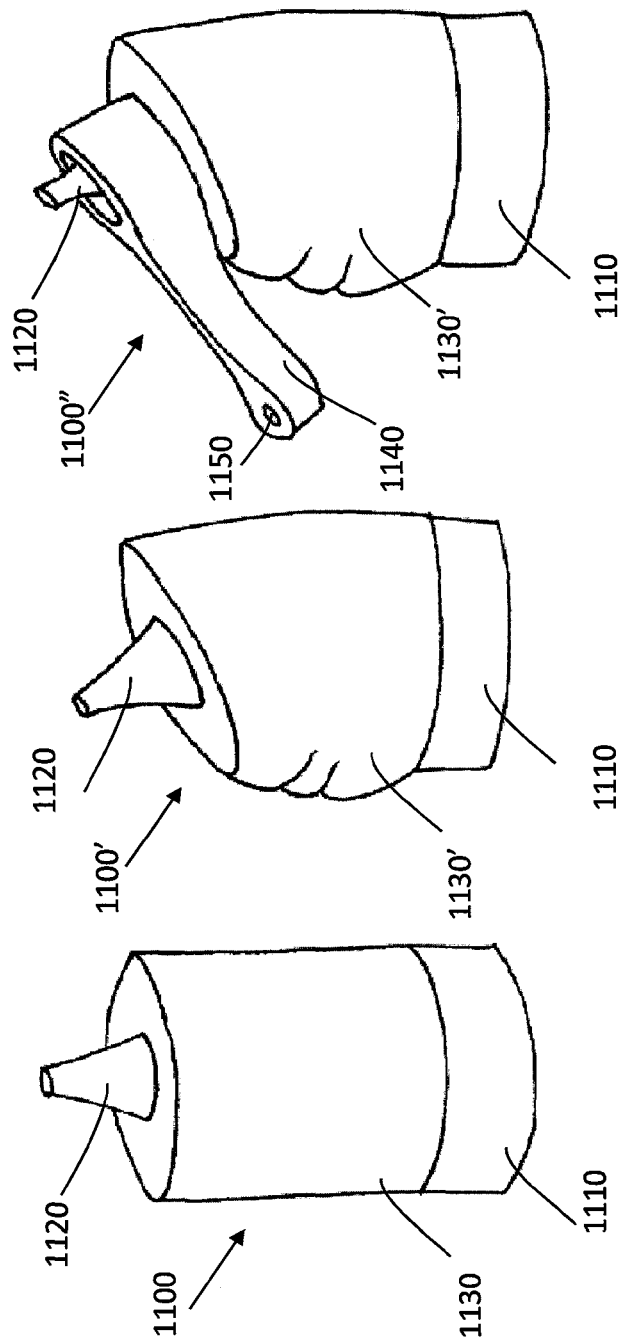
FIG. 12*a* schematically illustrates a template before deformation in accordance with an exemplary embodiment.
FIG. 12*b* schematically illustrates the template shown in FIG. 12*a* after deformation.
FIG. 12*c* schematically illustrates the deformed embodiment shown in FIG. 12*b* provided with an accessory for a trajectory.

Reference is now made to FIGS. 12a-12c illustrating a template before deforming, after deforming and with an accessory for finding the trajectory, respectively. FIG. 12a shows an example of a template that is totally built from one bulk of plastic material that softens and cures into a final rigid shape according to methods described earlier. It is shown that the template in its generic form, have a base of the template which will at end attach to the anchoring points or anchoring structure of the medical device, and at the same time will be directly or indirectly be attached to a robot base or arm; 1120 is the portion of the template that connects to the medical device or to an arm that connects to the medical device; 1130 is the plastic bulk to be deformed. After template 1100 is inserted in the robot, the robot will deform it as required according to methods described herein before. This is shown in FIG. 12b showing how the bulk of the plastic material is now of a different shape 1100' aligning portion 1120 relative to base 1110; after which a medical device 1140 which is shown in FIG. 12c is attached to. Alternatively, 1140 could be a handle that the medical device attaches to at attachment location 1150. it is important to note that in this example trajectory of medical device into the body does not pass through template base 1110.

It is another aspect of the invention in which base 1110 can also be part of the plastic bulk, it will be shaped to its required shape by pressing the plastic bulk against a pattern held by the robot base. This will form a pattern in the base of the template which mates correctly with the anchoring points or anchoring element so that when cured operational guide 1100' will become rigid and be ready for use.

Figure 13:
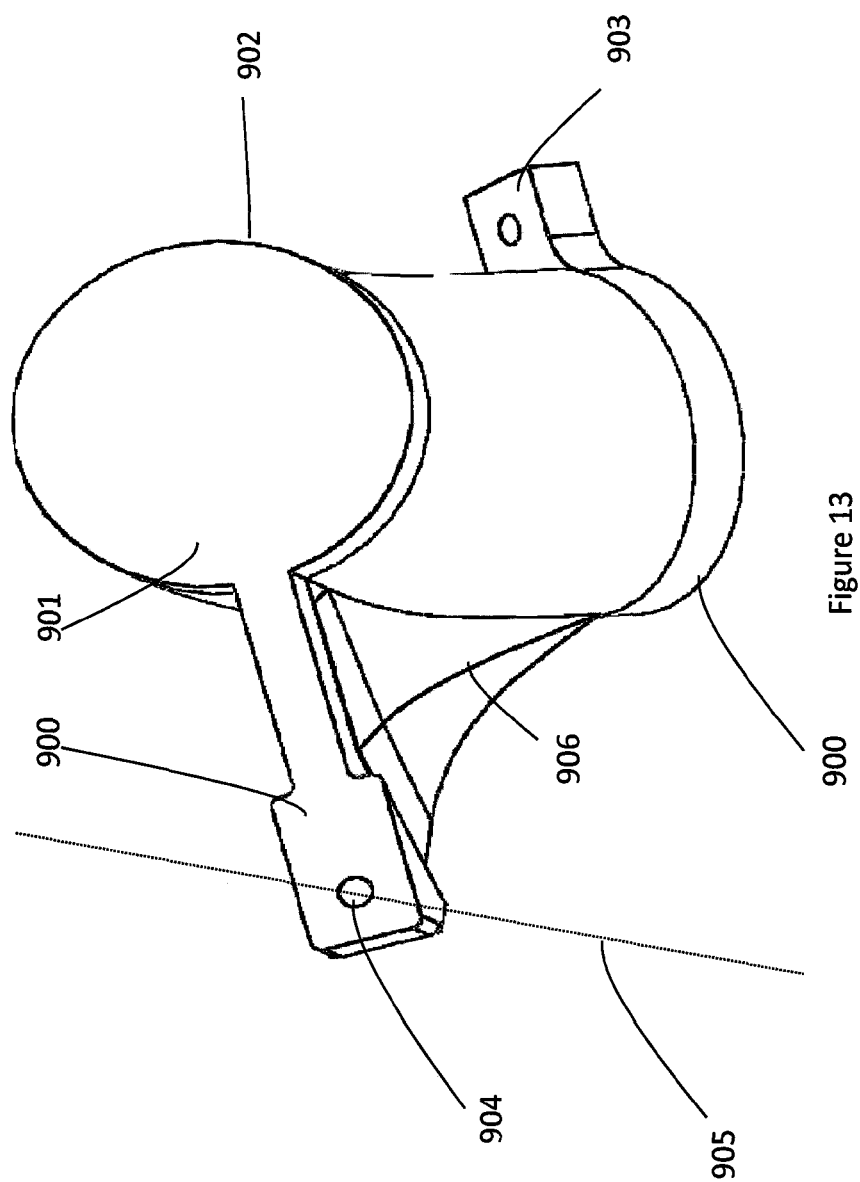
FIG. 13 schematically illustrates another embodiment of a surgical guide in its operational form.

Reference is now made to FIG. 13 illustrating another embodiment of a surgical guide in its operational form where trajectory 905 of the medical device passes to the body and does not pass through the base of the template. In such cases, the medical device will sit and attach to a mating place on arm 900 in place 904. In such cases, forces activated on the medical device or on the arm will lead to structural force moments that might lead to bending of the arm, tearing of the arm from the structure tearing of the base from the attachment structure or attachment points. For this connecting elements 906 are also supplied connecting the arms with the base distributing the forces to the operational guide base, In other examples, these connecting elements between the upper arms and the base could be another mechanically adjusting arm instead of plastic material that cure. 901 is where the arm attaches to the upper side of the template, the upper side 902 of template where forces may tear the upper side of the template or the arm from the template body during the operational template use. 903 shows reinforced base of template on counter side of the arm with some engagement mechanism strengthening the hold of the template to the anchoring structure. 904 shows medical device attachment and mating portion of the handle, 905 show the trajectory of the medical device not passing through the base of the template, 906 shows connecting structure that supports the arm by distributing the forces encountered by the arm to the template base.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

The scope of the present invention is defined by the appended claims and includes both combinations and sub combinations of the various features described hereinabove as well as variations and modifications thereof, which would occur to persons skilled in the art upon reading the foregoing description.

The invention claimed is:

1. A kit comprising:
   a medical guide template comprising a plurality of components, wherein the medical guide template has a malleable prefixed structural configuration, enabling at least some of the plurality of components to be moved relative to each other with multiple degrees of freedom; and
   a sterile receptacle enclosing the medical guide template, wherein the medical guide template, while being enclosed within the sterile receptacle, is configured to be deformed into an operational medical guide having a desired and fixed structural configuration, and
   wherein at least some of the plurality of components are configured to be moved during deformation.

2. The kit of claim 1, wherein said medical guide template comprises curable adhesive material located in joints between the plurality of components.

3. The kit of claim 1, wherein the operational medical guide is adapted to allow a medical device to be aligned with a target or trajectory identified on an image of a treatment area.

4. The kit of claim 1, wherein the medical guide template is configured to be turned into a malleable phase prior to its deformation.

5. The kit of claim 1, wherein the medical guide template is inherently malleable.

6. The kit of claim 1, wherein the medical guide template is made of or comprises a curable material.

7. The kit of claim 1, wherein the medical guide template is configured to become malleable by irradiation, heating, cooling, electric current, electric induction, or any combination thereof.

8. The kit of claim 1, wherein the medical guide template comprises a curable adhesive located in joints between the plurality of components.

9. The kit of claim 1, wherein the receptacle is configured to maintain sterility of the medical guide template before and after deformation.

10. The kit of claim 1, wherein the operational medical guide is configured to facilitate or assist in delivery of at least one medical device to a target area along one or more trajectories defined by the fixed structural configuration of the operational medical guide.

11. The kit of claim 1, wherein the operational medical guide is configured to juxtapose or space apart bones.

12. The kit of claim 1, wherein some of the plurality of components include non-deformable parts, wherein the medical guide template comprises articles of low heat-conductivity configured to isolate the non-deformable parts.

13. The kit of claim 1, wherein the medical guide template comprises a locking mechanism configured to lock the operational medical guide in its fixed configuration.

14. The kit of claim 1, wherein the sterile receptacle comprises an external and an internal attachment element configured to be coupled to the medical guide template and assist in the deformation of the medical guide template into the operational medical guide.

15. The kit of claim 1, wherein said medical guide template is a curable template bulk.

16. The kit of claim 15, wherein said curable template bulk is cured using UV light.

17. The kit of claim 1, wherein the operational medical guide further comprises:
   at least one base element configured to directly or indirectly engage body anchoring points;
   at least one targeting element, configured to directly or indirectly engage at least one medical device; and
   at least one connective structural element connecting the at least one base element with the at least one targeting element,
   wherein the operational medical guide is configured to allow at least one medical device to access at least one target area when the at least one base element is engaged with the body anchoring points so that the at least one medical device is engaged with the at least one targeting element, and
   wherein the at least one connective structural element is configured to be deformed.

18. The kit of claim 17, wherein the deformation is based upon fiducial-points for the operational medical guide engagement, and
   wherein the operational medical guide is configured to be attached to body anchoring points, the anchoring points being in a measured relationship to the fiducial-points.

19. A system comprising:
   at least one marker;
   a computer;
   a scanner;
   a forming robot;
   a medical malleable guide template;
   a sterile receptacle enclosing the guide template; and
   a medical device,
   wherein the at least one marker represents physical reference points,
   wherein the scanner is configured to scan a bodily part with the at least one marker thereon,
   wherein the computer is operationally coupled to the scanner and the forming robot, and wherein the computer is configured to:

receive an image from the scanner,
establish a relationship between the at least one marker and a target or trajectory identified on the image, and
establish forming data transferred to the forming robot;
wherein the robot is configured to deform the template into an operational medical guide having a desired and fixed structural configuration, while being enclosed in the sterile receptacle, such that sterility of the medical guide template is maintained during deformation;
wherein the deformation comprises moving at least some of the plurality of components relative to each other.

\* \* \* \* \*